(12) United States Patent
Fujii et al.

(10) Patent No.: US 9,366,608 B2
(45) Date of Patent: Jun. 14, 2016

(54) TENSILE TEST MACHINE

(71) Applicant: NATIONAL UNIVERSITY CORPORATION SHIZUOKA UNIVERSITY, Shizuoka (JP)

(72) Inventors: Tomoyuki Fujii, Kosai (JP); Keiichiro Tohgo, Hamamatsu (JP); Yoshinobu Shimamura, Hamamatsu (JP)

(73) Assignee: National University Corporation Shizuoka University, Shizuoka-shi (JP)

( * ) Notice: Subject to any disclaimer, the term of this patent is extended or adjusted under 35 U.S.C. 154(b) by 0 days.

(21) Appl. No.: 14/363,308

(22) PCT Filed: Dec. 4, 2012

(86) PCT No.: PCT/JP2012/081330
§ 371 (c)(1),
(2) Date: Jun. 6, 2014

(87) PCT Pub. No.: WO2013/084861
PCT Pub. Date: Jun. 13, 2013

(65) Prior Publication Data
US 2015/0177112 A1 Jun. 25, 2015

(30) Foreign Application Priority Data

Dec. 7, 2011 (JP) ................................ 2011-268295

(51) Int. Cl.
*G01N 3/08* (2006.01)
(52) U.S. Cl.
CPC .......... *G01N 3/08* (2013.01); *G01N 2203/0017* (2013.01)
(58) Field of Classification Search
CPC ............. G01L 5/00; G01L 25/00; G01N 3/08
USPC .................................................. 73/830, 831
See application file for complete search history.

(56) References Cited

U.S. PATENT DOCUMENTS

| 3,815,929 | A | * | 6/1974 | Steinberger | ........... | B23B 31/302 |
| | | | | | | 279/4.02 |
| 4,064,745 | A | * | 12/1977 | Gaddum | .................. | G01N 3/32 |
| | | | | | | 73/805 |
| 4,711,587 | A | * | 12/1987 | Cocito | ..................... | G01N 3/22 |
| | | | | | | 374/16 |
| 4,924,709 | A | | 5/1990 | Plyter | .............................. | 73/829 |
| 5,305,645 | A | * | 4/1994 | Reifsnider | ............... | G01N 3/32 |
| | | | | | | 73/808 |
| 7,520,182 | B2 | * | 4/2009 | Takamura | ............. | G01L 3/1457 |
| | | | | | | 73/862.08 |

FOREIGN PATENT DOCUMENTS

| GB | 2101749 | 1/1983 |
| JP | 06003234 | 1/1994 |
| JP | 2000002636 | 1/2000 |
| JP | 2005249612 | 9/2005 |
| JP | 2005338026 | 12/2005 |

* cited by examiner

*Primary Examiner* — Lisa Caputo
*Assistant Examiner* — Octavia Hollington
(74) *Attorney, Agent, or Firm* — Michael Tobias (57) ABSTRACT

A tensile test machine which has a simple structure and which can measure the strength of a sample having a minute tensile strength is provided. The tensile test machine 100 has a first gripping member 117 and a second gripping member 125 which oppose each other in the horizontal direction and grip two end portions of a sample WK. The first gripping member 117 is supported by a moment receiving member 113*a* of a torque meter 113 through a first support beam 116 and a tensile force transmitting member 115. The tensile force transmitting member 115 is formed so as to extend in the radial direction of the moment receiving member 113*a*. The second gripping member 125 is supported by a displacement table 121 through a second support beam 124 and a gripping member support base 123. It is displaced in the direction away from the first gripping member 117, and the amount of displacement is measured by a displacement measuring device 128. An external computer 130 measures the tensile strength of the sample WK using the tensile force sensed by the torque meter 113 and the amount of displacement of the second gripping member 125 sensed by the displacement measuring device 128.

12 Claims, 4 Drawing Sheets

TENSILE TEST MACHINE

TECHNICAL FIELD

This invention relates to a tensile test machine for evaluating the mechanical strength of a sample by applying a tensile force to the sample.

BACKGROUND ART

From in the past, tensile test machines for measuring various mechanical properties of a sample by applying a tensile force to the sample have existed. For example, below-described Patent Document 1 discloses a tensile test machine which measures the tensile strength of a sample by fixing one end of a ribbon-shaped sample in place and applying a tensile force to the other end of the sample through a load cell.

PRIOR ART DOCUMENTS

Patent Documents

Patent Document 1: JP 06-3234 A

However, the tensile test machine described in above-mentioned Patent Document 1 has the problem that even when the tensile force is within the capacity of the load cell, even minute variations in the tensile force cause the accuracy of measurement to become unstable. This is because the load resolution of the load cell is a prescribed resolution corresponding to the maximum load. Therefore, when carrying out strength measurement on a sample having a tensile strength of the mN order such as a fiber, a foil, or a membrane, it is necessary to use a special tensile test machine employing an expensive load cell having a high load resolution. Namely, a conventional tensile test machine had the problem that carrying out strength measurement of samples having a minute tensile strength imposed a large economic burden.

SUMMARY OF THE INVENTION

The present invention was made in order to cope with the above-described problems, and its object is to provide a tensile test machine which has a simple structure and can carry out tensile strength measurement on a sample having a minute tensile strength.

In order to achieve this object, the present invention set forth in claim 1 is characterized by comprising a pair of gripping members which grip two different end portions of a sample on opposite sides of the sample in the horizontal direction, a tensile force applying means which applies a tensile force to the sample through the pair of gripping members, a torque meter which has a moment receiving member for receiving a torsional moment and which outputs an electrical signal corresponding to the torsional moment applied to the moment receiving member, and a tensile force transmitting member which extends in the radial direction of the central axis of the moment receiving member from the moment receiving member and supports one gripping member of the pair of gripping members.

Due to this characteristic of the present invention set forth in claim 1 which is constituted in this manner, one gripping member of a pair of gripping members which grip two different end portions of a sample on opposite sides of the sample in the horizontal direction is supported by a tensile force transmitting member which is connected to a moment receiving member of a torque meter and which extends in the radial direction of the moment receiving member. Therefore, the tensile force which is applied to the sample is amplified in accordance with the length of the tensile force transmitting member and acts on the moment receiving member. Namely, a tensile test machine according to the present invention amplifies the force which acts on the moment receiving member of a torque meter in accordance with the length of the tensile force transmitting member, so accurate strength measurement can be carried out even when the tensile strength of the sample is extremely small. In other words, a tensile test machine according to the present invention can prescribe the load resolution of a torque meter by the length of the tensile force transmitting member. As a result, the tensile test machine can perform strength measurement of a sample having a very low tensile strength with a simple structure. In addition, a tensile test machine according to the present invention applies a tensile force to a sample in the horizontal direction, so strength measurement of the sample can be accurately performed while preventing elongation or breakage of the sample due to tensile force caused by the weight of the sample or the weight of fixtures or the like for supporting the sample.

Another characteristic of the present invention which is set forth in claim 2 is that the tensile force transmitting member of the tensile test machine rotatably supports the one of the gripping members.

Due to this other characteristic of the present invention set forth in claim 2 which is constituted in this manner, the tensile force transmitting member in the tensile test machine rotatably supports a gripping member. As a result, even when one or both of the gripping members of the pair of gripping members undergoes relative displacement when a tensile force is applied to the sample and the direction of tensile force acting on the sample changes, the gripping member which is supported by the tensile force transmitting member rotationally displaces so as to match the direction of application of tensile force applied to the sample. As a result, damage to the sample due to bending thereof when measuring the tensile strength of the sample is prevented, and an accurate tensile test can be carried out. By also rotatably supporting the other gripping member of the pair of gripping members so that the gripped portion of the sample can rotate, the above-described damage to the sample gripped by the other gripping member can be prevented.

Another characteristic of the present invention which is set forth in claim 3 is that the tensile force transmitting member in the tensile test machine is detachably connected to the moment receiving member.

Due to this other characteristic of the present invention set forth in claim 3 which is constituted in this manner, the tensile force transmitting member in the tensile test machine is detachably connected to the moment receiving member of the torque meter. As a result, the tensile test machine enables the tensile force transmitting member to be replaced by a different one. Namely, by replacing the tensile force transmitting member with one having a length and material corresponding to the tensile strength of the sample undergoing strength measurement, the tensile test machine can cope with a wide range of types of samples. In this case, the tensile force transmitting member may have a structure such that it detachably supports the gripping member. As a result, the tensile force transmitting member can cope with a wide range of types of sample by replacing the gripping member.

Another characteristic of the present invention which is set forth in claim 4 is that the tensile test machine further comprises a displacement measuring means which measures the relative amount of displacement of the pair of gripping members.

Due to this other characteristic of the present invention set forth in claim 4 which is constituted in this manner, the tensile test machine has a displacement measuring means which measures the amount of relative displacement of the pair of gripping members. As a result, the tensile test machine can measure the tensile strength based on a tensile force applied to a sample and the amount of displacement of the sample.

In this case, as set forth in claim 5, for example, the displacement measuring means of the tensile test machine can measure the relative amount of displacement of the pair of gripping members using the rotational angle of the moment receiving member and the length of the tensile force transmitting member between the moment receiving member and the one of the gripping members.

In these cases, as set forth in claim 6, the tensile force applying means of the tensile test machine may comprise a rotating shaft which is rotationally driven, and a rotational drive force transmitting member which is formed so as to extend in the radial direction from the rotating shaft and which supports the one or the other of the pair of gripping members, and a tensile force can be applied to the sample by the rotational drive force of the rotating shaft which is transmitted by the rotational drive force transmitting member.

Another characteristic of the present invention which is set forth in claim 7 is that the tensile test machine further comprises a gripping member displacement means which displaces the one of the gripping members in a direction perpendicular to the direction of application of tensile force by the tensile force applying means.

Due to this other characteristic of the present invention set forth in claim 7 which is constituted in this manner, the tensile test machine comprises a gripping member displacement means which displaces the gripping member in a direction perpendicular to the direction of application of a tensile force to the gripping member by the tensile force applying displacement means. In this case, the gripping member displacement means may displace the gripping member with respect to the tensile force transmitting member, or it may displace the gripping member by displacing the tensile force transmitting member, or it can displace the tensile force transmitting member and the gripping member by displacing the torque meter. As a result, the tensile test machine can grip a sample supported by the pair of gripping members in a straight line by displacing the gripping member without bending the sample, and the direction in which a tensile force is applied to the sample can be made perpendicular to the radial direction of the central axis of the moment receiving member of the torque meter. As a result, tensile force can be efficiently transmitted to the moment receiving member of the torque meter, and the tensile test machine can accurately carry out strength measurement of a sample.

Another characteristic of the present invention which is set forth in claim 8 is that the tensile test machine comprises a rotational displacement regulating means which regulates the rotational displacement of the moment receiving member of the torque meter.

Due to this other characteristic of the present invention set forth in claim 8 which is constituted in this manner, the tensile test machine has a rotational displacement regulating means which regulates the rotational displacement of the moment receiving member of the torque meter. As a result, the tensile test machine can regulate rotation of the moment receiving member when an excessive tensile force is applied to the moment receiving member of the torque meter, and damage to the torque meter can be prevented.

Another characteristics of the present invention which is set forth in claim 9 is that the torque meter of the tensile test machine has a perpendicularity maintaining means which produces rotational displacement of the moment receiving member so that the tensile force transmitting member is perpendicular to the direction of application of a tensile force by the tensile force applying means.

Due to this other characteristic of the present invention set forth in claim 9 which is constituted in this manner, the tensile test machine comprises a perpendicularity maintaining means which rotationally displaces the moment receiving member so that the tensile force transmitting member is perpendicular to the direction of application of tensile force by the tensile force applying means. Therefore, when a tensile force is applied to a sample, the tensile test machine can rotationally drive the moment receiving member so that the tensile force transmitting member always remains perpendicular to the direction of application of tensile force when the tensile force transmitting member attempts to rotate around the central axis of the moment receiving member. As a result, a tensile test of a sample can be carried out in a state in which the tensile force transmitting member is always perpendicular to the direction of application of a tensile force, so strength measurement of a sample can be accurately carried out. An AC servo motor which can rotationally drive the moment receiving member can be used as the torque meter.

MODES FOR CARRYING OUT THE INVENTION

Figure 1:
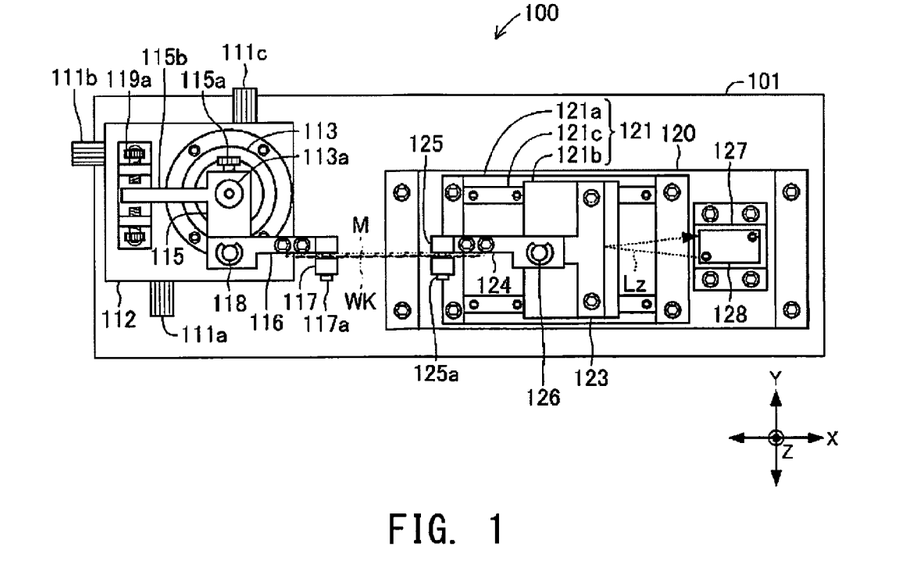
FIG. 1 is a plan view schematically showing the exterior of a tensile test machine according to the present invention.
Figure 2:
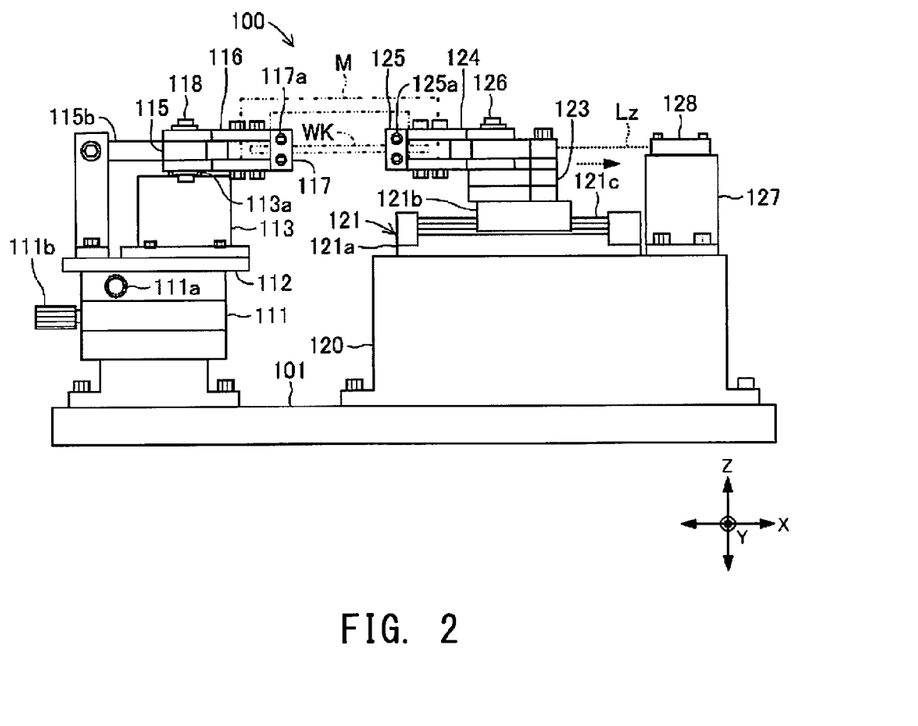
FIG. 2 is a front view schematically showing the exterior of the tensile test machine shown in FIG. 1.
Figure 3:
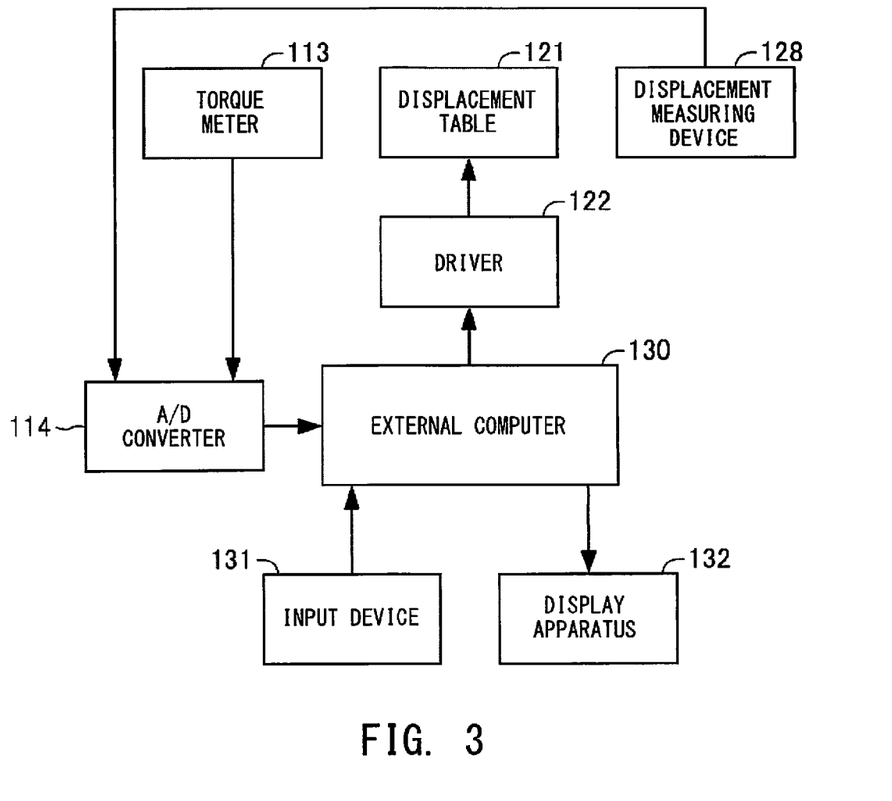
FIG. 3 is a block diagram of a control system for controlling the operation of the tensile test machine shown in FIG. 1.

Below, a mode for carrying out a tensile test machine according to the present invention will be explained while referring to the drawings. FIG. 1 is a plan view schematically showing the exterior of a tensile test machine 100 according to the present invention. FIG. 2 is a front view schematically showing the exterior of the tensile test machine 100 shown in FIG. 1. FIG. 3 is a block diagram of a control system for controlling the operation of the tensile test machine 100. The figures referred to in this description are schematically illustrated with some components exaggerated for ease of understanding the present invention. Therefore, the dimensions, proportions, and the like of the components may differ from the actual dimensions, proportions, etc. This tensile test machine 100 is a measuring apparatus which applies a tensile force to a sample WK which is primarily a fiber, a foil, or a film and measures the tensile strength of the sample WK.

Structure of the Tensile Test Machine 100

The tensile test machine 100 has a base 101. The base 101 is a plate-shaped member primarily for supporting the mechanical components of the tensile test machine 100. It is formed from a steel plate which has a roughly rectangular shape as viewed in plan and which extends in the x-axis direction in the figures (to the left and right in the figures). A torque meter support base 110 (not shown in FIG. 1) is secured atop the left hand side of the base 101 in the figures. The torque meter support base 110 is a steel base for supporting a torque meter 113 through a gripping member displacement stage 111, and it is formed so as to extend in the shape of a pillar in the z-axis direction (upwards in the figures) from the base 101. The gripping member displacement stage 111 is secured on the top surface of the torque meter support base 110.

The gripping member displacement stage 111 is a movable table having a top surface which can be displaced in the x-axis direction, the y-axis direction, and the z-axis direction in the figures. Operating knobs 111a, 111b, and 111c which are operated by hand to displace the top surface of the gripping member displacement stage 111 in the x-axis direction, the y-axis direction, and the z-axis direction, respectively, are provided on the side surfaces of the gripping member displacement stage 111. In addition, the torque meter 113 and a rotation limiting pillar 119 are secured through a support plate 112 on the top surface of the gripping member displacement stage 111. The support plate 112 is a steel plate-shaped member for supporting the torque meter 113 and the rotation limiting pillar 119.

The torque meter 113 has a moment receiving member 113a having the shape of a round rod for receiving a torsional moment. The torque meter 113 is a sensor which converts a torsional moment which is applied to the moment receiving member 113a into an electrical signal by means of an unillustrated strain gauge which is glued to the surface of the moment receiving member 113a and outputs the signal. In this embodiment, the torque meter 113 can measure a load of up to 500 nN-m. The torque meter 113 is secured to the top surface of the gripping member displacement stage 111 through the support plate 112, and it outputs an electrical signal corresponding to the torsional moment applied to the moment receiving member 113a to an external computer 130 to which it is connected through an A/D converter 114. The A/D converter 114 is an electronic circuit which converts analog electrical signals which are output from the torque meter 113 and a below-described displacement measuring device 128 into digital electrical signals and outputs them to the external computer 130.

A tensile force transmitting member 115 is connected to the moment receiving member 113a of the torque meter 113. The tensile force transmitting member 115 is a rod-shaped member made of steel which extends from the moment receiving member 113a of the torque meter 113 in the radial direction from the central axis of the moment receiving member 113a. In other words, it extends outwards in the direction of a transverse cross section (in the y-axis direction in the figure). One end of the tensile force transmitting member 115 is connected to the moment receiving member 113a of the torque meter 113 and is supported by the moment receiving member 113a, and the other end is connected to a first gripping member 117 through a first support beam 116 and supports the first gripping member 117. The tensile force transmitting member 115 and the moment receiving member 113a of the torque meter 113 are securely connected to each other by a set screw 115a in a state in which the moment receiving member 113a passes through a through hole formed in the tensile force transmitting member 115. In other words, the tensile force transmitting member 115 is detachably connected to the moment receiving member 113a of the torque meter 113 by the set screw 115a.

The first support beam 116, which is connected to the other end of the tensile force transmitting member 115, is constituted by two plate-shaped members made of steel which extend in parallel from the tensile force transmitting member 115 in the x-axis direction in the figures. The first gripping member 117 is supported at its end portion. The first support beam 116 is connected to the tensile force transmitting member 115 by a connecting pin 118 and is supported so as to be able to rotate with respect to the tensile force transmitting member 115. Namely, in a state in which the first support beam 116 extends in the x-axis direction in the figures perpendicular to the tensile force transmitting member 115, the first support beam 116 supports the first gripping member 117 so as to be able to rotate with respect to the tensile force transmitting member 115. The rotational center of the first support beam 116 on the tensile force transmitting member 115 and a gripped position at which the sample WK is gripped by the first gripping member 117 are positioned on the same line in the x-axis direction in the figure. In this embodiment, the distance between the center of the through hole in the tensile force transmitting member 115 through which the moment receiving member 113a of the torque meter 113 passes and the center of the through hole in the tensile force transmitting member 115 through which the connecting pin 118 passes is set to 18 mm.

The first gripping member 117 is a member which grips one end of the sample WK from opposite sides. It is constituted so as to releasably grip the sample WK by making two opposing block-shaped members contact or separate from each other depending upon the state of tightening of mounting bolts 117a. Namely, the tensile force transmitting member 115 has the function of transmitting the torsional moment which depends on the tensile force applied to the sample WK and the length of the tensile force transmitting member 115 to the moment receiving member 113a of the torque meter 113.

The tensile force transmitting member 115 has a rotation limiting member 115b which extends in the x-axis direction from the left side surface thereof. The rotation limiting member 115b is a member for regulating excessive rotational displacement of the moment receiving member 113a of the torque meter 113 together with the rotation limiting pillar 119. The rotation limiting pillar 119 is a pillar-shaped member made of steel for preventing excessive rotational displacement of the moment receiving member 113a of the torque meter 113 together with the rotation limiting member 115b. It extends upwards from the support plate 112 and is bifurcated so that its end portions sandwich the rotation limiting member 115b of the tensile force transmitting member 115. The two end portions of the rotation limiting pillar 119 which is bifurcated each have a displacement regulating bolt 119a for regulating the amount of rotational displacement of the rotation limiting member 115b between the two end portions.

A displacement table support base 120 is secured atop the right side of the base 101 in the figure. The displacement table support base 120 is a steel base for supporting a displacement table 121 and the displacement measuring device 128. It extends in the shape of a pillar in the z-axis direction (upwards in the figures) from the base 101. The displacement table 121 is a movable mounting base which supports the second gripping member 125 and displaces it in the direction towards or away from the first gripping member 117. It is constituted primarily by a bed portion 121a and a table portion 121b.

Of these portions, the bed portion 121a is constituted by a linear motion guide 121c which extends in the x-axis direction and an unillustrated stator coil and linear encoder head. The bed portion 121a is secured to the top surface of the displacement table support base 120. The table portion 121b is constituted by an unillustrated linear motion block, a magnet (made of neodymium), and a linear encoder scale. It is supported atop the bed portion 121a. The linear motion block is able to slide along the linear motion guide 121c, whereby the table portion 121b is supported so as to be able to displace back and forth in the x-axis direction. The displacement table 121 is connected to the external computer 130 through a driver 122, and its operation is controlled by a control program which is made by the external computer 130 and stored inside the driver 122. Thus, in this embodiment, the displacement table 121 comprises a so-called linear motor table.

A gripping member support base 123 is secured atop the table portion 121b of the displacement table 121. The gripping member support base 123, which is secured atop the table portion 121b, is a member made of steel for supporting the second gripping member 125 through a second support beam 124 such that the second gripping member 125 opposes the first gripping member 117. The second support beam 124 comprises two plate-shaped members made of steel which extend in parallel to each other in the x-axis direction from the gripping member support base 123. The end portion of the second support beam 124 supports the second gripping member 125.

The second support beam 124 is connected to the gripping member support base 123 by a connecting pin 126, and it is supported so as to be able to rotate with respect to the gripping member support base 123. Namely, the second support beam 124 supports the second gripping member 125 so as to be able to rotate with respect to the gripping member support base 123 in a state in which the second support beam 124 extends in the x-axis direction. The rotational center of the second support beam 124 on the gripping member support base 123 and a gripped position at which the sample WK is gripped by the second gripping member 125 are positioned on the same line in the x-axis direction. In addition, the rotational center and the gripped position are positioned on the same line in the x-axis direction as the rotational center of the first support beam 117 on the tensile force transmitting member 115 and the gripped position at which the sample WK is gripped by first gripping member 117.

The second gripping member 125 is a member which grips the other end of the sample WK from opposite sides. It is constituted such that two opposing block members are contacted or separated by changing the degree of tightening of mounting bolts 125a to releasably grip the sample WK. Namely, the first gripping member 117 and the second gripping member 125 constitute a pair of gripping members which oppose each other in the horizontal direction and which grip both ends of a sample WK from the horizontal direction.

A measuring device support base 127 is secured to the top surface of the displacement table support base 120 on the right-hand side of the displacement table 121 in the figures, and a displacement measuring device 128 is provided on the measuring device support base 127. The displacement measuring device 128 is an optical measuring device which optically measures the amount of displacement of the second gripping member 125 by measuring the amount of displacement of the gripping member support base 123. More specifically, the displacement measuring device 128 measures the amount of displacement of the gripping member support base 123 using triangulation in which a laser beam $L_z$ (shown by a dashed line) is irradiated towards the back surface of the gripping member support base 123, the laser beam $L_z$ which is reflected from the back surface is received, and the displacement measuring device 128 outputs an electrical signal indicating the amount of displacement. The displacement measuring device 128 is connected to the external computer 130 through the A/D converter 114, and its operation is controlled by the external computer 130.

The external computer 130 is constituted by a microcomputer comprising a CPU, a ROM, a RAM, a hard disk, and the like. It executes an unillustrated tensile strength measurement program in accordance with instructions from an input device 131 such as a keyboard or a mouse to measure the tensile strength of a sample WK. More specifically, when the external computer 130 displaces the table portion 121b of the displacement table 121 through the driver 122, the electrical signals which are output from the torque meter 113 and the displacement measuring device 128 are input to the external computer 130 through the A/D converter 114, and the external computer 130 carries out prescribed processing to measure the tensile strength of the sample WK.

The external computer 130 has a display apparatus 132 comprising a liquid crystal display for displaying the operating state of the external computer 130 and the results of the strength measurement of the sample WK. In this embodiment, the external computer 130 is assumed to be a personal computer, but as long as it is a type which can perform each of the above-described functions, it can of course be another type of computer.

Operation of the Tensile Test Machine 100

Figure 4:
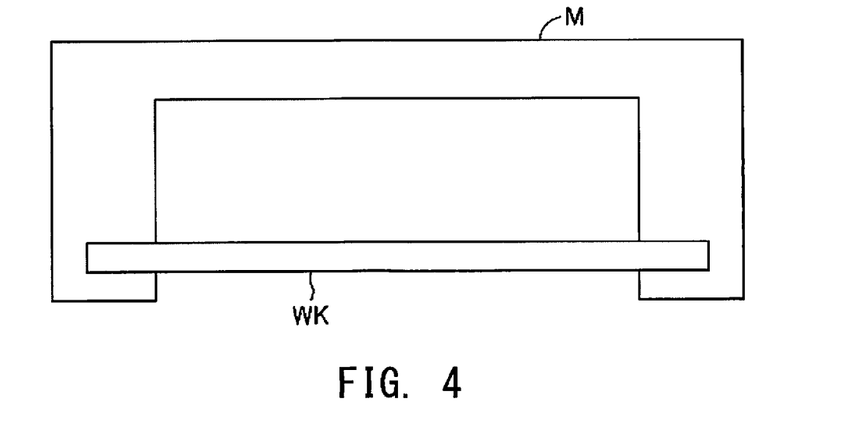
FIG. 4 is a front view showing a state in which a sample gripped by the tensile test machine shown in FIG. 1 is secured to a mat.

Next, the operation of the tensile test machine 100 which has the above-described structure will be explained. First, a user prepares a sample WK. In this embodiment, as shown in FIG. 4, the sample WK is a ribbon-shaped piece of aluminum foil having a thickness of approximately 10 micrometers, a length of approximately 30 mm, and a width of approximately 5 mm. In this case, the user supports the ribbon-shaped aluminum foil sample WK by gluing both end portions to a paper mat M. As a result, the sample WK, which has extremely low stiffness, can be held by the tensile test machine 100 without being deformed or damaged. In FIG. 1 and FIG. 2, a sample WK supported by a mat M is shown by a two-dot chain line.

Next, the user turns on the power supplies of the tensile test machine 100 and the external computer 130, and then he sets the sample WK on the tensile test machine 100. Specifically, the user grips both end portions of the sample WK supported by the mat M with the first gripping member 117 and the second gripping member 125. In a state in which one end portion of the portion of the sample WK inside of the mat M is gripped by the second gripping member 125, the user displaces the table portion 121b of the displacement table 121 in the x-axis direction and grips the other end portion inside of the mat M with the first gripping member 117.

Next, the user manipulates operating knobs 111b and 111c of the gripping member displacement stage 111 to adjust the position of the first gripping member 117 in the y-axis direction and the z-axis direction and aligns it with the position of the opposing second gripping member 125, and he manipulates operating knob 111a to adjust the position of the first gripping member 117 in the x-axis direction so that the sample WK, which is supported by the first gripping member 117 and the second gripping member 125, extends in a straight line without being bent. Next, the user cuts the mat M in two at a suitable location with scissors or the like. As a result, the sample WK is set in the tensile test machine 100 such that a tensile test is possible. Namely, the separation between the first gripping member 117 and the second gripping member 125 when the sample WK is set in the tensile test machine 100 becomes a gauge length.

Next, the user carries out a tensile test on the sample WK. Specifically, the user operates the input device 131 of the external computer 130 to start displacement of the table portion 121b of the displacement table 121 through the driver 122. At this time, the user inputs to the driver 122 the direction, amount, and speed of displacement of the table portion 121b of the displacement table 121. As a result, the second gripping member 125 starts to displace in a direction away from the first gripping member 117 due to the start of displacement of the table portion 121a of the displacement table 121 (see the dashed line arrow in FIG. 2).

The tensile force applied to the sample WK by displacement of the second gripping member 125 is transmitted to the moment receiving member 113a of the torque meter 113 through the first gripping member 117, the first support beam 116, and the tensile force transmitting member 115. A torsional moment equal to the vector product of the tensile force applied to the sample WK and the length of the tensile force transmitting member 115 acts on the moment receiving member 113a of the torque meter 113. Therefore, even when a minute tensile force acts on the sample WK, strain can be produced in the moment receiving member 113a, and the torque meter 113 outputs an electrical signal corresponding to the strain.

The first gripping member 117 and the second gripping member 125 which grip the sample WK are rotatably connected to the tensile force transmitting member 115 and the gripping member support beams 123 by connecting pins 118 and 126, respectively. Therefore, even when flexural deformation of the tensile force transmitting member 115 occurs due to application of a tensile force and/or the direction of displacement of the table portion 121b of the displacement table 121 deviates from the lengthwise direction of the sample WK, the first gripping member 117 and the second gripping member 125 pivot so that the lengthwise direction of the sample WK and the direction of application of the tensile force coincide, so the tensile test can continue with good accuracy without damage to the sample WK.

The displacement measuring device 128 which is disposed next to the displacement table 121 produces an output corresponding to the amount of displacement of the table portion 112b of the displacement table 112. As a result, the external computer 130 collects the electrical signal from the torque meter 113 and the electrical signal from the displacement measuring device 128 which are continuously input through the A/D converter 114, namely, electrical signals which indicate a torsional moment (torque) which is applied to the moment receiving member 113a of the torque meter 113 and the amount of displacement of the second gripping member 125. Accordingly, the external computer 130 calculates and stores the tensile force applied to the sample WK based on electrical signals indicating the torsional moment applied to the moment receiving member 113a, and it calculates and stores the amount of elongation of the sample WK based on the electrical signal indicating the amount of displacement of the second gripping member 125.

When calculating the amount of elongation of the sample WK, the external computer 130 makes the amount of elongation of the sample WK the amount of displacement of the second gripping member 125 minus the amount of deformation in the x-axis direction of the tensile force transmitting member 115 due to the application of tensile force to the tensile force transmitting member 115 (namely, the amount of flexural deformation) and the amount of its displacement. In this case, the amount of deformation and the amount of displacement of the tensile force transmitting member 115 vary in accordance with the shape and the material of the tensile force transmitting member 115 and the moment receiving member 113a. Therefore, the user previously stores various parameters corresponding to the shape and the material of the tensile force transmitting member 115 and the moment receiving member 113a (such as the lengths, the modulus of longitudinal elasticity, the second moments of area, and the like of the tensile force transmitting member 115 and the moment receiving member 113a) in the external computer 130. When the tensile force applied to the sample WK is sufficiently small compared to the stiffness of the tensile force transmitting member 115 and the moment receiving member 113a, the amount of deformation and/or the amount of displacement of the tensile force transmitting member 115 can be ignored. In addition, when a tensile force applied to the sample WK is sufficiently small compared to the stiffness of the tensile force transmitting member 115 and the moment receiving member 113a, deformation in the x-axis direction of the tensile force transmitting member 115 (namely, flexural deformation) and displacement of the tensile force transmitting member 115 do not take place, and it is not necessary to take into consideration the amount of deformation and/or the amount of displacement of the tensile force transmitting member 115.

The tensile test of the sample WK is carried out until the sample WK breaks or until the table portion 121b of the displacement table 121 displaces by just a previously set amount of displacement. Accordingly, in the period until the sample WK breaks or the table portion 121b of the displacement table 121 displaces by just the set amount of displacement, the external computer 130 continuously stores the tensile force applied to the sample WK and the amount of elongation of the sample WK while displacing the table portion 121a of the displacement table 121.

When the external computer 130 senses that the sample WK has broken or that the table portion 121b of the displacement table 121 has displaced by just the set amount of displacement, it stops displacement of the table portion 121b of the displacement table 121 through the driver 122. Next, the external computer 130 displays the tensile force which was applied to the sample WK and the amount of elongation of the sample WK which were stored, or information indicating mechanical properties of the sample WK which was calculated based on the above information (such as a stress-strain curve, the elastic limit, the coefficient of elasticity, or the like) on the display apparatus 132. Accordingly, the user can evaluate the tensile strength of the sample WK based on this information displayed by the display apparatus 132. The user then completes a series of tensile test operations on the sample WK by removing the sample WK from the first gripping member 117 and the second gripping member 125.

As can be understood from the above description of operation, according to the above-described embodiment, in the tensile force test machine 100, the first gripping member 117 of the first gripping member 117 and the second gripping member 125, which are a pair of gripping members which grip two different end portions of a sample WK from the horizontal direction, is supported by the tensile force transmitting member 115 which is connected to the moment receiving member 113a of the torque meter 113 and extends in the radial direction of the central axis of the moment receiving member 113a. Therefore, the tensile force which is applied to the sample WK is amplified in accordance with the length of the tensile force transmitting member 115 and acts on the moment receiving member 113a of the torque meter 113. Namely, the tensile test machine 100 amplifies the force acting on the moment receiving member 113a of the torque meter 113 in accordance with the length of the tensile force transmitting member 115, so even when the tensile strength of the sample WK is extremely small, accurate strength measurement can be carried out. In other words, the tensile test machine 100 prescribes the load resolution of the torque meter 113 based on the length of the tensile force transmitting member 115. As a result, the tensile test machine 100 can carry out strength measurement of a sample WK having a very small tensile strength with a simple structure. In addition, a tensile test machine 100 according to the present invention applies a tensile force to a sample WK in the horizontal direction, so it is possible to accurately carrying out strength measurement of a sample WK while preventing elongation or breakage of the sample WK due to tensile force caused by the weight of the sample WK or the weight of fixtures or the like for holding the sample WK.

Figure 5:
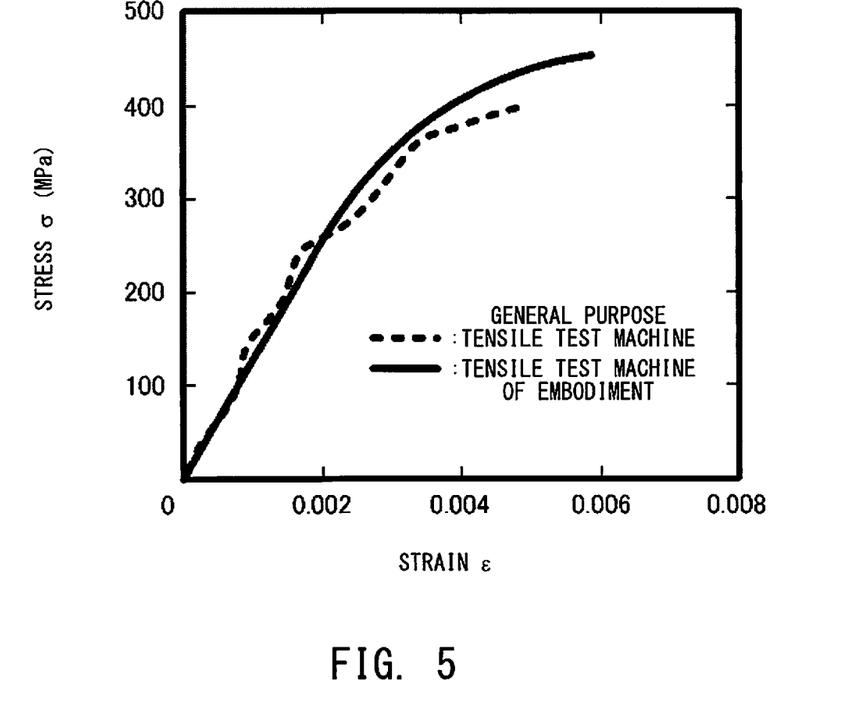
FIG. 5 is a stress-strain diagram showing the results of a tensile test of a sample by a tensile test machine according to the present invention and a conventional general purpose tensile test machine.

The present inventors ascertained the accuracy and reproducibility of a tensile test by a tensile test machine 100 according to the present invention by carrying out a tensile test using a tensile test machine 100 according to the present invention and a conventional general purpose tensile test machine (not shown) employing a load cell. Specifically, the present inventors carried out a tensile test using a tensile test machine 100 according to the present invention and a conventional general purpose tensile test machine on a sample WK in the form of a copper foil with a thickness of 5 micrometers. FIG. 5 shows a stress-strain diagram for tensile tests carried out using a tensile test machine 100 according to the present invention and the conventional general purpose tensile test machine. In FIG. 5, the solid line shows the test results for the conventional general purpose test machine, and the dashed line shows the test results for the tensile test machine 100 according to the present invention.

From these test results (experimental results), it can be seen that the stress-strain diagram for the tensile test machine 100 according to the present invention and the stress-strain diagram for the conventional general purpose tensile test machine, namely, the trends for the behavior in deformation of a sample WK were nearly the same. The tests were carried out multiple times (10 times), and the same tendency occurred each time. Accordingly, it can be said that accuracy which is comparable to that of the conventional general purpose tensile test machine could be exhibited with good reproducibility. The rated torque of the torque meter 113 used in this experiment was 500 mN-m, and its resolution was ±0.1%. The length of the tensile force transmitting member 115 used in the experiment was 18 mm. Therefore, it was confirmed from the following Equation 1 that a load resolution of approximately 30 mN could be guaranteed by the tensile test machine 100 of this embodiment.

$$0.5 \text{ mN-m}/0.018 \text{ m} = 27.7 \text{ mN} \qquad \text{Equation 1}$$

A person carrying out the present invention is not limited to the above-described embodiment, and a variety of variations are possible as long as they achieve the object of the present invention. In the below-described variations, the same components as in the above-described embodiment of a tensile test machine 100 are indicated by the same or corresponding reference numbers as for the tensile test machine 100, so an explanation of those components will be omitted.

Figure 6:
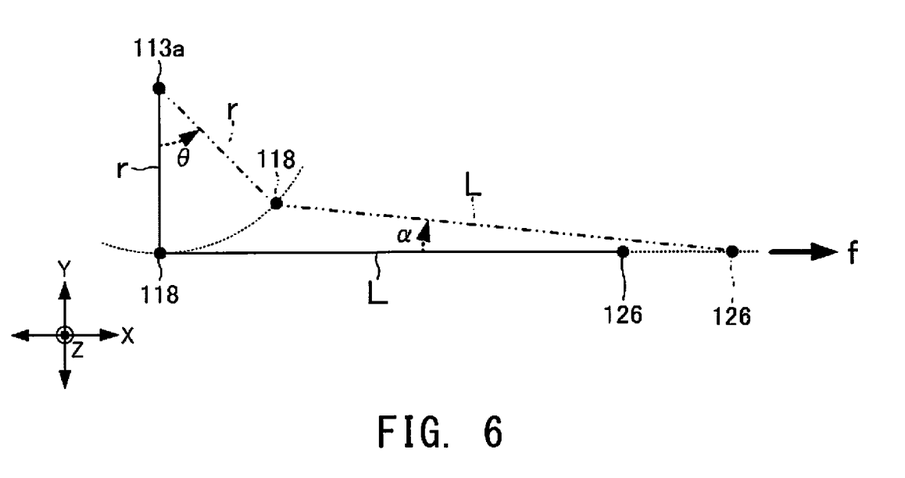
FIG. 6 is an explanatory view for explaining the principles of correcting the tensile force acting on a sample.

In the above-described embodiment, no consideration is given to the rotational displacement of the moment receiving member 113a of the torque meter 113 when a tensile force acts on the sample WK. This is because the tensile force applied to the sample WK is so very small that these rotational displacements can be ignored. However, it is also possible to take into consideration the rotational displacement of the moment receiving member 113a when a tensile force acts on the sample WK. Specifically, as shown in FIG. 6, for example, when the second gripping member 125 moves away from the first gripping member 117 at the time of strength measurement of the sample WK, when the tensile force transmitting member 115 is rotationally displaced by just an angle θ (degrees) in the x-axis direction and the y-axis direction with the moment receiving member 113a as a center, the torsional moment N can be found by the correcting equations given by the following Equation 2 or the following Equation 3.

$$N = r \times f \times \cos(\theta) \times \cos(\alpha)$$
$$= r \times f \times \cos(\theta) \times \sin^{-1}[(r - r \times \cos(\theta))/L] \qquad \text{Equation 2}$$

$$N = r \times f \times \cos(\theta) \times [1 - \{(r - r \times \cos(\theta))/L\}^2]^{1/2} \qquad \text{Equation 3}$$

Here, r is the distance between the rotational center of the moment receiving member 113a and the rotational center of the connecting pin 118, namely, the length of the arm of the tensile force transmitting member 115, f is the size of the tensile force produced by the displacement table 121, and L is the distance between the rotational center of connecting pin 118 and connecting pin 126 including the sample WK. θ is the angle of displacement of the moment receiving member 113a of the torque meter 113, or the angle of displacement of the torque meter 113 itself when that displacement angle is obtainable (torque sensing by the difference in the phase of rotation). α is the rotational angle of a straight line between connecting pin 118 and connecting pin 126 after the moment receiving member 113a of the torque meter 113 undergoes rotational displacement by angle of displacement θ compared to before the moment receiving member 113a undergoes rotational displacement. In other words, it is the angle of displacement of the line of action of tensile force applied to the sample WK. With this information, it is possible to calculate the tensile force f from the torsional moment N taking into consideration the rotational displacement of the tensile force transmitting member 115, and the mechanical strength of the sample WK can be more accurately measured.

When the angle of displacement θ of the moment receiving member 113a of the torque meter 113 is zero or so small that it can be ignored, the tensile force f can be calculated from the torsional moment N by below-described Equation 4. In this case, θ equals zero, so cos(θ) equals 1, and Equation 4 becomes Equation 5. Therefore, the torsional moment N is determined by the product of r and L.

$$N = r \times f \times \cos(\theta) \qquad \text{Equation 4}$$

$$N = r \times f \qquad \text{Equation 5}$$

The tensile test machine 100 can be constituted so that the angle of displacement θ of the moment receiving member 113a is always zero. Specifically, a torque meter 113 is used which has the ability to rotationally displace the moment receiving member 113a. For example, a servo motor such as an AC servo motor or a brushless DC servo motor can be used as the torque meter 113. In this case, the external computer 130 receives the angle of displacement θ of the moment receiving member 113a from the torque meter 113 in the form of a servo motor, and it rotationally drives the moment receiving member 113a (the rotating shaft of the servo motor) so that the angle of displacement θ becomes zero. In addition, the external computer 130 can specify the size of the torsional moment applied to the tensile force transmitting member 115 in accordance with the electric current which rotationally drives the moment receiving member 113a of the torque meter 113, and it can specify the amount of elongation of the sample WK by the amount of displacement of the table portion 112b of the displacement table 112 as determined by the displacement measuring device 128.

Namely, when a tensile force is applied to the sample WK in the tensile test machine 100, when the tensile force transmitting member 115 attempts to rotate about the central axis of the moment receiving member 113a, the moment receiving member 113a can be rotationally driven so that the tensile force transmitting member 115 and the direction of action of tensile force are always maintained perpendicular to each other. As a result, a tensile test of the sample WK can be carried out in a state in which the tensile force transmitting member 115 and the direction of action of tensile force are always maintained perpendicular to each other, whereby strength measurement of the sample WK can be accurately carried out. Namely, a torque meter 113 in the form of a servo motor corresponds to a perpendicularity maintaining means according to the present invention.

Instead of a torque meter 113 in the form of a servo motor, a perpendicularity maintaining means can be constituted by providing a sensor which senses the angle of displacement θ of the moment receiving member 113a or the tensile force transmitting member 115, and a servo motor which rotationally displaces the torque meter 113 so that the angle of displacement θ which is sensed by the sensor becomes zero can be separately provided. In this case, θ equals zero, so the tensile force f can be found from above-described Equation 5.

In the above-described embodiment, the first gripping member 117 and the second gripping member 125 in the tensile test machine 100 are constituted so that the second gripping member 125 is displaced with respect to the first gripping member 117. Namely, the displacement table 121 corresponds to a tensile force applying means according to the present invention. However, it is sufficient for the tensile force applying means to be constituted such that the pair of gripping members comprising the first gripping member 117 and the second gripping member 125 undergo relative displacement away from each other. Namely, the tensile force applying means can be constituted so that the second gripping member 125 is fixed in place and the first gripping member 117 is displaced with respect to the stationary second gripping member 125. In addition, the tensile force applying means can be constituted so that the first gripping member 117 and the second gripping member 125 are both displaced in the direction away from each other.

Figure 7:
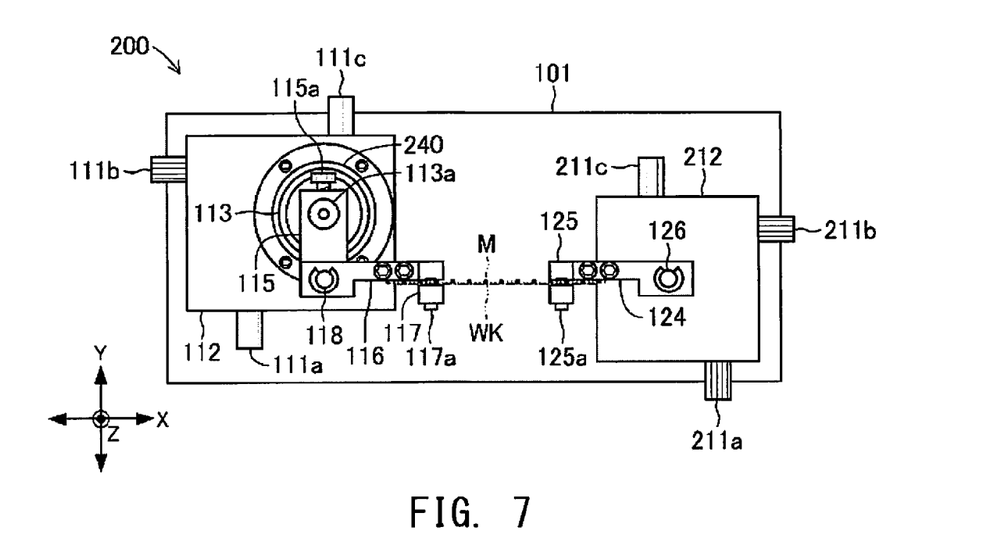
FIG. 7 is a plan view schematically showing the exterior of a tensile test machine according to a variation of the present invention.

For example, FIG. 7 shows a tensile test machine 200 which is constituted such that the second gripping member 125 is secured against displacement and the first gripping member 117 is displaced with respect to the stationary second gripping member 125. In this tensile test machine 200, a support plate 212 similar to support plate 112 is secured atop a gripping member displacement stage 211 having a structure similar to gripping member displacement stage 111, and the second gripping member 125 is rotatably supported on the support plate 212 by a connecting pin 126. In this case, the gripping member displacement stage 211 is a movable table for adjusting the position of the second gripping member 125, and it is secured so as not to displace with respect to the base 101.

The first gripping member 117 is supported by a servo motor 240 which is disposed between the gripping member displacement stage 111 and the torque meter 113. The servo motor 240 is an electric motor which rotationally drives the first gripping member 117 together with the torque meter 113 with the moment receiving member 113a as a rotational center. Its operation is controlled by the external computer 130.

An AC servo motor or a DC servo motor, for example, can be used as the servo motor 240. As shown in FIG. 7, the torque meter 113 and the servo motor 240 can be coaxially disposed and connected with each other, but it is also possible for them to be connected with each other on different axial lines by a rotating mechanism (such as a gear mechanism, a pulley and belt mechanism, or a rotating shaft). The servo motor 240 can be one which can detect the rotational angle and torque. It is also possible to use an electric motor other than a servo motor 240 such as an inverter-controlled synchronous motor, a stepping motor, or a direct current motor as an actuator for rotationally driving the first gripping member 117.

With a tensile test machine 200 which is constituted in this manner, due to the rotational drive by the servo motor 240, the first gripping member 117 is rotationally displaced together with the torque meter 113 and the tensile force transmitting member 115 with the moment receiving member 113a as a center of rotation. Namely, in this tensile test machine 200, a torque meter 113 and a servo motor 240 as a tensile force applying means are provided for the first gripping member 117, so the structure of the tensile test machine 200 can be simple and compact.

In the above-described embodiment, the tensile force applying means is constituted by a displacement table 121 comprising a linear motor table. However, the tensile force applying means is not limited to the above-described embodiment as long as a tensile force can be applied to the sample WK through the first gripping member 117 and the second gripping member 125. For example, the servo motor 240 shown in the above-described variation can be used as a tensile force applying means.

Figure 8:
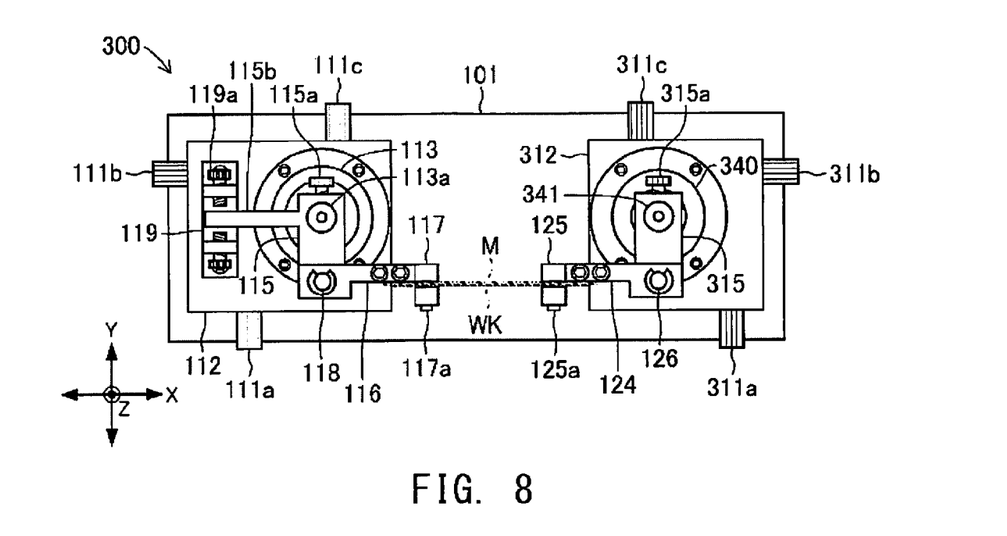
FIG. 8 is a plan view schematically showing the exterior of a tensile test machine according to another variation of the present invention.

As an example, FIG. 8 shows a tensile test machine 300 which is constituted such that the second gripping member 125 is rotationally displaced by a servo motor 340. This tensile test machine 300 is constituted such that a support plate 312 which is similar to support plate 212 is secured atop a gripping member displacement stage 311 which is similar to above-described gripping member displacement stage 211, and the servo motor 340 which has a structure like above-described servo motor 240 is secured atop the support plate 312. A tensile force transmitting member 315 having a structure like tensile force transmitting member 115 is secured to a rotating drive shaft 341 of the servo motor 340, and the second gripping member 125 is rotatably connected to the end of the tensile force transmitting member 315 by a connecting pin 126. With a tensile test machine 300 having this structure, the rotational drive force of the servo motor 340 is amplified by the tension transmitting member 315, and the second gripping member 125 is rotationally displaced, so a tensile force can be applied to the sample WK with a smaller force.

In this tensile test machine 300, even when the length of the arm of tensile force transmitting member 115 is different from the length of the arm of tensile force transmitting member 315, by using the correction equations given by Equations 2 or 3, a more accurate tensile force can be calculated. Namely, even when the length of the arm of tensile force transmitting member 115 is different from the length of the arm of tensile force transmitting member 315, the tensile test machine 300 can accurately measure the mechanical strength of the sample WK. When the length of the arm of tensile force transmitting member 115 and the length of the arm of tensile force transmitting member 315 are the same or can be considered to be the same, the sample WK is pulled parallel to the x-axis direction, so the angle of rotation a shown in FIG. 6 becomes zero. Therefore, correction using the correction equations given by Equation 2 or Equation 3 becomes simpler, and the tensile force f can be determined using Equation 4.

In the above-described embodiment, the length of the so-called arm which applies a torsional moment to the moment receiving member 113a is the length between the center of the through hole in the tensile force transmitting member 115 through which the moment receiving member 113a of the torque meter 113 passes and the center of the through hole through which the connecting pin 118 passes, which in the present embodiment is 18 mm. However, the length of this arm is suitably set in accordance with the tensile strength of the sample WK. In this case, the length of the arm which applies a torsional moment to the moment receiving member 113a can be set based not only on the length of the tensile force transmitting member 115 but also on the gripping position of the sample WK by the first gripping member 117. Namely, in a tensile test machine in accordance with the present invention, the load resolution and the maximum measurable load of the torque meter 113 can be adjusted by the length of this arm.

In the above-described embodiment, the structure is such that a tensile force is applied to the sample WK in a state in which the tensile force transmitting member 115 and the first support beam 116 are perpendicular to each other. As a result, the tensile force which is applied to the sample WK can be efficiently transmitted to the moment receiving member 113a of the torque meter 113. However, it is possible to measure the strength of the sample WK even if a tensile force is applied in a state in which the relationship between the tensile force transmitting member 115 and the first support beam 116 is an acute angle or an obtuse angle. As a result, the length of the arm can be increased, and strength measurement of a sample WK having a lower tensile strength can be carried out.

In the above-described embodiment, the tensile force transmitting member 115 is detachably supported by the moment receiving member 113a of the torque meter 113, and it detachably supports the first gripping member 117. As a result, the tensile test machine 100 makes it possible to replace the tensile force transmitting member 115 in accordance with the type of sample WK or the tensile force applied to the sample WK. The tensile test machine 100 also makes it possible to replace the tensile force transmitting member 115 when the tensile force transmitting member 115 is damaged. However, when it is not necessary to replace the tensile force transmitting member 115, the tensile force transmitting member 115 may be fixedly supported by the moment receiving member 113a of the torque meter 113, and it may fixedly support the first gripping member 117. In addition, the tensile force transmitting member 115 is not limited to a rectangular rod, and other shapes, such as a round rod, are of course possible.

In the above-described embodiment, the tensile test machine 100 has a structure which includes a displacement measuring device 128 in order to measure the amount of displacement of the second gripping member 125 for measuring the amount of elongation of the sample WK. Namely, the displacement measuring device 128 corresponds to a displacement measuring means according to the present invention. However, when it is not necessary to measure the amount of elongation of the sample WK, the tensile test machine 100 may have a structure which omits the displacement measuring device 128.

In the above-described embodiment, the tensile test machine 100 has a structure which includes a gripping member displacement stage 111 for displacing the first gripping member 117 in the x-axis direction, the y-axis direction, and the z-axis direction in the figures. As a result, the tensile test machine 100 adjusts the position of the first gripping member 117 in the y-axis direction and the z-axis direction and aligns it with the position of the second gripping member 125, and it adjusts the position of the first gripping member 117 in the x-axis direction and stretches the sample WK which is supported by the first gripping member 117 and the second gripping member 125 in a straight line. However, when it is not necessary to adjust the position of the first gripping member 117, such as when the positional relationship between the first gripping member 117 and the second gripping member 125 is previously prescribed, the tensile test machine 100 can have a structure which omits the gripping member displacement stage 111.

The gripping member displacement stage 111 corresponds to a gripping member displacement means according to the present invention in that it can displace the first gripping member 117 in the y-axis direction and the z-axis direction, namely, in the directions perpendicular to the direction of tensile force applied to the sample WK. Accordingly, as long as the gripping member displacement stage 111 has a structure such that it can displace the position of at least the first gripping member 117 in a direction perpendicular to the direction of action of a tensile force applied to the sample WK, and specifically so that it can displace the first gripping member 117 in the y-axis direction and the z-axis direction, it can adjust the position of the first gripping member 117 in the y-axis direction and the z-axis direction. Namely, by having a gripping member displacement means, the tensile test machine 100 can carry out a tensile test on a sample WK by replacing the tensile force transmitting member 115 with ones having different arm lengths and/or replacing the first gripping member 117 with different first gripping members.

In the above-described embodiment of a tensile test machine 100, the first gripping member 117 and the second gripping member 125 are rotatably connected to the tensile force transmitting member 115 and the gripping member support base 123. However, the tensile test machine 100 can carry out strength measurement of a sample WK even if the first gripping member 117 and the second gripping member 125 are rigidly connected to the tensile force transmitting member 115 and the gripping member support base 123 so as to be unable to rotate.

In the above-described embodiment, the tensile force transmitting member 115 which applies a torsional moment to the moment receiving member 113a of the torque meter 113 has the shape of a rod. However, as long as the tensile force transmitting member 115 has a shape such that it amplifies the tensile force applied to the sample WK and transmits it to the moment receiving member 113a, namely, as long as it has a shape which extends radially from the moment receiving member 113a, it is not limited to the shape in the above-described embodiment. For example, the tensile force transmitting member 115 can be formed in the shape of a plate (such as a disc) which extends in the radial direction of the moment receiving member 113a, and the first gripping member 117 can be directly connected to the plate-shaped member, or indirectly connected to the plate-shaped member through the first support beam 116, at any position in the radial direction on the surface of the plate-shaped member. In this case, with the plate-shaped tensile force transmitting member 115, by having the first gripping member 117 detachable at a plurality of locations in the radial direction of the moment receiving member 113a, the length of the arm of the tensile force transmitting member 115 can be easily varied, and the load resolution or the maximum measurable load can be varied. The radial direction of the moment receiving member 113a means a direction in a transverse cross section of the moment receiving member 113a, and it does not mean that the moment receiving member 113a is limited to a round rod. Namely, the moment receiving member 113a can of course be a square rod.

In the above-described embodiment, the tensile test machine 100 has a structure in which a rotation limiting member 115b is provided on the first gripping member 117, and a rotation limiting pillar 119 is provided on the torque meter support base 110. As a result, the tensile test machine 100 can regulate excessive rotational displacement of the moment receiving member 113a of the torque meter 113, and damage to the torque meter 113 can be prevented. Namely, the rotation limiting member 115b and the rotation limiting pillar 119 correspond to a rotational displacement regulating means according to the present invention. However, as long as the rotational displacement regulating means can regulate the rotational displacement of the moment receiving member 113a of the torque meter 113, it is not necessarily limited to the structure in the above-described embodiment. In addition, when it is not necessary to regulate the rotational displacement of the moment receiving member 113a of the torque meter 113, the rotation limiting member 115b and the rotation limiting pillar 119, i.e., the rotational displacement regulating means may be omitted from the tensile test machine 100.

EXPLANATION OF SYMBOLS

WK: sample
M: mat
$L_z$: laser beam
100, 200, 300: tensile test machine
101: base
110: torque meter support base
111, 211: gripping member displacement stage
111a, 111b, 111c, 211a, 211b, 211c: operating knob
112, 212, 312: support plate
113: torque meter
113a: moment receiving member
114: A/D converter
115, 315: tensile force transmitting member
115a, 315a: set screw
115b: rotation limiting member
116: first support beam
117: first gripping member
117a: mounting bolt
118: connecting pin
119: rotation limiting pillar
119a: displacement regulating bolt
120: displacement table support base
121: displacement table
121a: bed portion
121b: table portion
121c: linear motion guide
122: driver
123: gripping member support base
124: second support beam
125: second gripping member
125a: mounting bolt
126: connecting pin
127: measuring device support base
128: displacement measuring device
130: external computer
131: input device
132: display apparatus
240, 340: servo motor

The invention claimed is:

1. A tensile test machine comprising:
first and second gripping members which grip two different end portions of a sample on opposite sides of the sample in the horizontal direction,
a tensile force applying means which applies a tensile force to the sample through one of the gripping members,
a torque meter which has a moment receiving member for receiving a torsional moment and which outputs an electrical signal corresponding to the torsional moment applied to the moment receiving member,
a tensile force transmitting member which extends in the radial direction of the central axis of the moment receiving member from the moment receiving member, and
a support beam which supports the first gripping member and is rotatably connected to the tensile force transmitting member at a location spaced from the central axis of the moment receiving member in the radial direction of the central axis.

2. A tensile test machine as claimed in claim 1, wherein the tensile force transmitting member is detachably connected to the moment receiving member.

3. A tensile test machine as claimed in claim 1, further comprising a displacement measuring means which measures the relative amount of displacement of the gripping members relative to each other.

4. A tensile test machine as claimed in claim 3, wherein the displacement measuring means measures the relative amount of displacement of the gripping members using the rotational angle of the moment receiving member and the distance between the central axis of the moment receiving member and the location where the support member is rotatably connected to the tensile force transmitting member.

5. A tensile test machine as claimed in claim 4, wherein the tensile force applying means comprises a rotating shaft which is rotationally driven, and a rotational drive force transmitting member which extends in the radial direction from the rotating shaft and supports one of the gripping members, and the tensile force is applied to the sample by the rotational drive force of the rotating shaft which is transmitted by the rotational drive force transmitting member.

6. A tensile test machine as claimed in claim 1, further comprising a gripping member displacement means which displaces the first gripping member in a direction perpendicular to the direction of application of tensile force by the tensile force applying means.

7. A tensile test machine as claimed in claim 6 wherein the gripping member displacement means comprises a displacement stage.

8. A tensile test machine as claimed in claim 1, further comprising a rotational displacement regulating means which regulates the rotational displacement of the moment receiving member of the torque meter.

9. A tensile test machine as claimed in claim 1, wherein the torque meter has a perpendicularity maintaining means which produces rotational displacement of the moment receiving member so that the tensile force transmitting member is perpendicular to the direction of application of tensile force by the tensile force applying means.

10. A tensile test machine as claimed in claim 1 wherein the torque meter comprises a rotary servo motor.

11. A tensile test machine as claimed in claim 1 wherein the tensile force applying means comprises a linear motor table.

12. A tensile test machine as claimed in claim 1 wherein the tensile force applying means comprises a servo motor which rotates the torque meter about the central axis of the moment receiving member.

* * * * *

UNITED STATES PATENT AND TRADEMARK OFFICE
CERTIFICATE OF CORRECTION

PATENT NO.       : 9,366,608 B2  
APPLICATION NO.  : 14/363308  
DATED            : June 14, 2016  
INVENTOR(S)      : Tomoyuki Fujii et al.

Page 1 of 1

It is certified that error appears in the above-identified patent and that said Letters Patent is hereby corrected as shown below:

In the claims  
Column 18, line 34 (claim 5, line 1), change "claim 4" to --claim 3--.

Signed and Sealed this  
Twelfth Day of July, 2016

Michelle K. Lee  
*Director of the United States Patent and Trademark Office*